United States Patent [19]
Morris et al.

[11] 3,948,962
[45] Apr. 6, 1976

[54] IRIDIUM CARBONYL COMPLEXES

[75] Inventors: Donald E. Morris, Kirkwood, Mo.; Harold Burnham Tinker, Zurich, Switzerland

[73] Assignee: Monsanto Company, St. Louis, Mo.

[22] Filed: Aug. 19, 1974

[21] Appl. No.: 498,335

[52] U.S. Cl. ...... 260/429 R; 252/431 R; 252/431 P; 260/413; 260/429 CY; 260/683.2; 260/683.65; 260/683.9
[51] Int. Cl.² .......................................... C07F 15/00
[58] Field of Search .......... 260/429 R, 429 CY, 429

[56] References Cited
UNITED STATES PATENTS
3,579,551   5/1971   Craddock et al. .................. 260/413

OTHER PUBLICATIONS
Stone et al., Advances in Organometallic Chemistry, Academic Press, N.Y., Vol. 8, pp. 155–157 (1970).

*Primary Examiner*—Helen M. S. Sneed

[57] ABSTRACT

The invention concerns novel compositions of matter having the formula

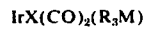

$IrX(CO)_2(R_3M)$ where $X = Cl, Br, I$, M is P, As, Sb, Bi and R is a $C_1$ to $C_{20}$ alkyl, alkoxy, aryl or aryloxy radical. There is also described herein a process for the preparation of these novel compounds. The compounds find use as hydrocarboxylation catalysts, especially in the absence of added halide promoters.

16 Claims, No Drawings

IRIDIUM CARBONYL COMPLEXES

This invention relates to novel carbonyl compounds of iridium and to processes for the preparation of these compounds.

More specifically, the invention is concerned with iridium complexes containing biphyllic ligands in the ratio of one biphyllic ligand per iridium.

Carbonyl compounds of iridium containing two, three, and four biphyllic ligands per iridium atom are well known in the art. Generally these compounds are formed by either; (1) refluxing a solution containing hydrated iridium trichloride and the biphyllic ligand (JACS, 83 (1961) 2784), or (2) the dehydrohalogenation of complexes of the type [IrHX$_2$(CO)(R$_3$M)$_2$] with a base such as sodium methoxide (J.Chem.Soc. (A), (1968)1887), or (3) the addition of the biphyllic ligand to solutions containing the anion, [IR(CO)$_2$X$_2$]$^-$ (J.Chem.Soc. (A), (1967) 604 and Inorg. Nucl. Chem. Letters, 5 (1969)433). In the past it has not been possible to prepare iridium carbonyl complexes containing one biphyllic ligand per iridium by any of these methods. The first method suffers from the fact that the reaction must always be conducted in the presence of excess biphyllic ligand and the products therefore, always contain two or more biphyllic ligands per iridium. Since the precursor in method 2 already contains two biphyllic ligands per iridium the product will always contain two biphyllic ligands per iridium atom. Method 3 offers the possibility of controlling the biphyllic ligand to iridium ratio. However, addition of biphyllic ligand to a solution containing [Ir(CO)$_2$X$_2$]$^-$ in a 1:1 molar ratio always yields a solution containing 50% of the bis-biphyllic ligand complex, e.g. IrX(CO)(R$_3$M)$_2$ or IrX(CO)$_2$(R$_3$M)$_2$, and 50% of the unreacted starting material, [Ir(CO)$_2$X$_2$]$^-$. From this one can infer that the rate of reaction of the second biphyllic ligand with the probable intermediate, [IrX$_2$(CO)(R$_3$M)]$^-$, [IrX$_2$(CO)$_2$(R$_3$M)]$^-$, or [IrX(CO)$_2$(R$_3$M)], is substantially faster than the rate of reaction of the first biphyllic ligand with [Ir(CO)$_2$X$_2$]$^-$.

Carbonyl compounds of iridium containing two, three, and four biphyllic ligands have found extensive use as catalysts for hydrogenation, hydroformylation, isomerization, and hydrosilylation reactions. Furthermore these same compounds as well as others which contain no biphyllic ligands, have been found to be extremely active catalysts for the hydrocarboxylation of olefins (U.S. Pat. No. 3,579,551) in the presence of iodide-containing promoters. The absence of these iodide promoters renders these compounds inactive for the hydrocarboxylation of olefins at the relatively mild conditions employed. Because of the corrosive nature of such iodide-promoted iridium catalysts which necessitates the use of expensive metals of construction for reactors, pumps, etc., it is desirable to eliminate the need for iodide promoters in these catalysts.

It is an object of the present invention to provide novel carbonyl complexes of iridium which contain biphyllic ligands in the molar ratio of one biphyllic ligand per iridium. The novel complexes of this invention are compounds represented by the formula

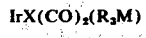
IrX(CO)$_2$(R$_3$M)

where X = Cl, Br, or I; M = P, As, Sb, or Bi; and R is a C$_1$ to C$_{20}$ alkyl, alkoxy, aryl, or aryloxy radical.

Another object of this invention is to provide processes for the preparation of said novel complexes. Still another object of this invention is to demonstrate the use of these novel complexes as hydrocarboxylation catalysts in the substantial absence of added halide promoters.

These and other objects of the invention will be apparent from the following detailed description.

The novel compounds of the invention are prepared by treating complexes of the type, [IrX(diene)(R$_3$M)], with one atmosphere of carbon monoxide at 25°C in a non-polar solvent such as petroleum ether. The preparation of the precursors, [IrX(diene)R$_3$M)], where X = Cl, Br, or I; R$_3$M = the biphyllic ligand as described above, and diene = a diolefin, have, in part, been described previously by Winckaus and Singer (Chem. Ber., 99 (1966)3610). Precursors having 1,5-cyclooctadiene (COD) as the diene have been particularly useful for the preparation of compounds of this invention. However, precursors containing other dienes, e.g. norbornadiene, duroquinone, cyclooctatetraene, 1,5-hexadiene, 1,3-cyclohexadiene, 2,5-dimethyl-1,5-hexadiene, etc., or even two mono-olefins, e.g., cyclooctene, cyclohexene, ethylene, etc., are also effective precursors for the preparation of the novel carbonyl compounds.

After treatment of the diene precursors with carbon monoxide for about ten minutes, the dicarbonyl monobiphyllic ligand iridium compounds have formed; they can then be isolated from the reaction solution, washed with petroleum ether, and air dried. Elemental analyses, infrared spectra (two terminal C-O stretching frequencies), and volumetric gas uptake measurements are all in agreement with the proposed formulation.

The yields of the products of the invention are dependent on the solvents employed. The products are very soluble in aromatic hydrocarbons such as benzene and toluene and consequently they are difficult to isolate from such solvents. It is necessary to add large volumes of paraffinic hydrocarbons to solutions of the products in these solvents to induce precipitation of the products. Even then the products are impure and the yields are low.

In more polar solvents such as chloroform, dichloromethane, 1,2-dichloroethane, acetone, etc., the desired dicarbonyl products are again produced. However, in these solvents, the products consume additional carbon monoxide and one isolates products which contain not two, but 2.5 carbon monoxides per iridium (in addition to 1 biphyllic ligand per iridium). These novel compounds will be discussed in more detail below.

In the preferred embodiment of the process for the preparation of the compounds of the invention, the solvent is petroleum ether. The products are only slightly soluble in this solvent thus making isolation easier. Since the precursors are also only slightly soluble the reaction is actually a heterogeneous reaction. Other paraffinic hydrocarbons such as hexane cyclohexane, or in general paraffins of 1 to 12 carbon atoms are also effective.

The preparative processes may be conveniently monitored by the use of volumetric carbon monoxide uptake measurements. In the majority of the cases in petroleum ether, exactly two moles of carbon monoxide are consumed per iridium atom. An exception to this is observed in the case when [IrI(COD)(Ph$_3$P)] is used as the precursor. In petroleum ether this precursor absorbs only one carbon monoxide per iridium to yield the novel monocarbonyl, [IrI(COD)(CO)(Ph$_3$P)]. However, in benzene this monocarbonyl, or the precursor, both yield [IrI(CO)$_2$(Ph$_3$P)] upon treatment with carbon monoxide.

The new compositions all contain carbonyl groups bound to the iridium atom and are conveniently characterized by an examination of their infrared spectra which show very strong C-O stretching frequencies. All of the dicarbonyl compounds exhibit two C-O bands at or near 2080 and 2000 cm$^{-1}$.

The novel dicarbonyl iridium complexes of this invention are ones which contain one biphyllic ligand per iridium. Suitable biphyllic ligands which comprise part of the iridium coordination complexes of this invention are those containing trivalent phosphorus, arsenic, antimony, and bismuth atoms and are referred to in this specification as phosphines, phosphites, arsines, arsenites, stibines, stibites, bismuthines, and bismuthites. In this group the individual phosphorus, arsenic, antimony, or bismuth atoms have one unshared pair of electrons available for bonding to the iridium atom. One, two, or three organic radicals, each having from one to twenty carbon atoms, may be bonded to the phosphorus, arsenic, antimony, or bismuth atom and the radicals are preferably selected from the group consisting of aryl, alkyl, aryloxy, or alkoxy groups. The latter two groups, viz. the aryloxy or alkoxy groups, contain an oxygen molecule between each organic radical and the phosphorus, arsenic, antimony, and bismuth atom. The preferred biphyllic ligands are those consisting of three organic groups bonded to each phosphorus, arsenic, antimony, or bismuth atom. For example, preferred biphyllic ligands are those illustrated by the following structural formulae R$_3$M where M is P, As, Sb, and B; and R is phenyl, phenoxy, tolyl, xylyl, dimethylphenyl, triethyl, etc.

The more preferred group includes the triarylphosphines, e.g. triphenylphosphine, tri-p-tolylphosphine; diarylmonoalkylphosphines, e.g. diphenylmethylphosphine; monoaryldialkylphosphines, e.g. phenyldimethylphosphine; triarylarsines, e.g. triphenylarsine; and triarylstibines, e.g. triphenylstibine.

In this specification the term biphyllic ligand is meant to refer only to monodentate ligands, i.e. ligands which contain only one phosphorus, arsenic, antimony, or bismuth atom per ligand molecule. It does not encompass ligands which contain two or more phosphorus, arsenic, antimony, or bismuth atoms per ligand molecule; i.e. molecules which can function as multidentate ligands.

Treatment of the IrX(diene)R$_3$M precursors with carbon monoxide in polar solvents such as chloroform, dichloromethane, etc. lead to novel ionic complexes containing 2.5 carbon monoxide ligands per iridium but still only one biphyllic ligand per iridium. There novel compounds have been characterized by volumetric carbon monoxide uptake, infrared spectroscopy, and conductivity measurements, as having the following general formula

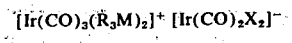
[Ir(CO)$_3$(R$_3$M)$_2$]$^+$ [Ir(CO)$_2$X$_2$]$^-$ where X, R, and M are as described above. These complex salts can also be prepared by mixing [Ir(CO)$_3$(R$_3$M)$_2$]$^+$BPh$_4$ with Ph$_4$As[Ir(CO)$_2$X$_2$]. In these complexes R$_3$M is a biphyllic ligand which fits the specifications described in the preceding paragraphs.

The following examples illustrate the specific embodiments of the invention but do not limit the scope of the invention. In these examples the following abbreviations are used: Ph = C$_6$H$_5$—, Me = CH$_3$—, Et = C$_2$H$_5$—, Bu = C$_4$H$_9$—, and COD = 1,5-cyclooctadiene.

EXAMPLE 1

Preparation of IrCl(CO)$_2$(Ph$_3$P)

A suspension of IrCl(COD)(Ph$_3$P) (0.4g) and petroleum ether (25 ml) is bubbled with carbon monoxide for 10 min. at 30°C. The resulting grey-green solids are filtered, washed with petroleum ether, and air dried (79% yield). Infrared analysis shows bands at 2085 (s) and 2002 (s) cm$^{-1}$ in CHCl$_3$.

Calcd. for IrCl(CO)$_2$(Ph$_3$P): C, 43.9; H, 2.77; P, 5.68; Cl, 6.51. Found: C, 42.8; H, 2.60; P, 5.92; Cl, 7.05.

EXAMPLE 2

Preparation of IrBr(CO)$_2$(Ph$_3$P)

A suspension of IrBr(COD)(Ph$_3$P) (0.9g) and hexane (25 ml) is bubbled with carbon monoxide for 10 min. at 25°C. The resulting blue-green solids are filtered, washed with petroleum ether, and air dried (100% yield). Infrared analysis shows bands at 2083 (s) and 2002 (s) cm$^{-1}$ in CHCl$_3$.

Calcd. for IrBr(CO)$_2$(Ph$_3$P): C, 40.68; H, 2.55; P, 5.24; Br, 13.53. Found: C, 41.63; H, 2.83; P, 5.09; Br, 12.79.

EXAMPLE 3

Preparation of IrI(CO)(COD)(Ph$_3$P)

A suspension of IrI(COD)(Ph$_3$P) (0.6g) and petroleum ether (15 ml) is bubbled with carbon monoxide for 10 min. The resulting ion solids were filtered, washed with petroleum ether, and air dried, (90% yield). Infrared analysis shows one band at 1987 (s) cm$^{-1}$ in CHCl$_3$.

Calcd. for IrI(CO)(COD)(Ph$_3$P): C, 45.19; H, 3.78; P, 4.31; I, 17.68. Found: C, 44.93; H, 3.86; P, 4.28; I, 17.13.

EXAMPLE 4

Preparation of IrI(CO)$_2$(Ph$_3$P)

A solution of IrI(COD)(Ph$_3$P) (0.3g) in benzene (25 ml) is bubbled with carbon monoxide for 10 min. Fifty ml of hexane is dripped into this solution to induce precipitation. The resulting brown solids are filtered, washed with petroleum ether, and air dried, (75% yield). Infrared analysis shows bands at 2078 (s) and 2000 (s) cm$^{-1}$ in CHCl$_3$.

Calcd. for IrI(CO)$_2$(Ph$_3$P): C, 37.68; H, 2.37; P, 4.85; I, 19.90. Found: C, 36.54; H, 2.54; P, 5.01; I, 19.51.

Instead of using benzene as the non-polar aromatic solvent good results are obtained when using toluene as the solvent.

Alternatively this complex can also be prepared by contacting IrI(CO)(COD)(Ph$_3$P) with carbon monoxide at one atmosphere in benzene. Addition of hexane followed by a similar work-up leads to an identical sample if IrI(CO)$_2$(Ph$_3$P).

EXAMPLE 5

Preparation of [Ir(CO)$_3$(Ph$_3$P)$_2$][Ir(CO)$_2$Cl$_2$]

A solution of IrCl(COD)(Ph$_3$P) (0.3 g) in dichloromethane (25 ml) is bubbled with carbon monoxide for 15 min. To the resulting solution was added petroleum ether (255 ml); grey solids precipitated. The solids were filtered, washed with petroleum ether, and air dried. (52% yield). Infrared analysis shows bands at 2082 (m), 2056 (m-s), 2017 (s) and 1975 (s) cm$^{-1}$ in $CHCl_3$.

Calcd. for $[Ir(CO)_3(Ph_3P)_2]^+[Ir(CO)_2Cl_2]^-$: C, 43.97; H, 2.69; Cl, 6.33; P, 5.53. Found: C, 43.00; H, 2.69; Cl, 6.25; P, 5.15.

Alternatively, $[Ir(CO)_3Ph_3P)_2]^+[Ir(CO)_2Cl_2]^-$ may be synthesized by the following procedure.

A solution of $Ph_4As[Ir(CO)_2Cl_2]$ (0.35 g) is CO-purged methanol (25 ml) was dripped into a 125 ml solution of $[Ir(CO)_3(Ph_3P)_2]^+BPh_4$ (0.56 g) is CO-purged methanol. The solids which formed were removed by filtration. The clear filtrate was concentrated under carbon monoxide. Grey solids were precipitated from this concentrated filtrate upon addition 265 ml of CO-purged ether. These solids were washed with ether and air dried, (44% yield). The infrared analysis and elemental analysis was very close to that obtained on the sample from the above synthesis.

Instead of dichloromethane as the polar solvent, good results are also obtained when using chloroform, 1,2-dichloroethane or acetone.

EXAMPLE 6

Preparation of $IrCl(CO)_2[(p-CH_3C_6H_4)_3P]$

A suspension of $IrCl(COD)[(CH_3C_6H_4)_3P](0.27g)$ in cyclohexane ether (10 ml) is bubbled with carbon monoxide for 10 min. The resulting purple solids were filtered, washed with petroleum ether, and air dried, (64% yield). Infrared analysis in $CHCl_3$ shows bands at 2079 (s) and 1999 (s) cm$^{-1}$.

Calcd. for $IrCl(CO)_2[(p-CH_3C_6H_4)_3P]$: C, 46.97; H, 3.59; P, 5.26; Cl, 6.02. Found: C, 47.95; H, 3.70; P, 5.23; Cl, 5.86.

EXAMPLE 7

Preparation of $IrCl(CO)_2(MePh_2P)$

A solution of $IrCl(COD)(MePh_2P)$ (0.57g) and petroleum ether (25 ml) is bubbled with carbon monoxide for 10 min. The resulting solution is cooled to 0°C and the brown precipitate which forms is filtered off and air dried, (23% yield). Infrared analysis in $CHCl_3$ shows bands at 2085 (s) and 2003 (s), cm$^{-1}$ Calcd. for $IrCl(CO)_2(MePh_2P)$: C, 37.23; H, 2.70; P, 6.40; Cl, 7.32. Found: C, 36.38; H, 2.92; P, 6.13; Cl, 7.39.

EXAMPLE 8

Preparation of $IrCl(CO)_2(Me_2PhP)$

A suspension of $IrCl(COD)(Me_2PhP)$ (0.43 g) and petroleum ether (25 ml) is bubbled with carbon monoxide for 10 min. The resulting yellow-green solids were filtered, washed with petroleum ether, and air dried (76% yield). Infrared analysis in $CHCl_3$ shows bands at 2084 (s) and 1999 (s) cm$^{-1}$.

Calcd. for $IrCl(CO)_2(Me_2PhP)$: C, 28.47; H, 2.62; P, 7.34; Cl, 8.40. Found: C, 28.56; H, 2.84; P, 7.27; Cl, 8.63.

EXAMPLE 9

Preparation of $IrCl(CO)_2(Ph_3As)$

A suspension of $IrCl(COD)(Ph_3As)$ (0.5g) and petroleum ether (25 ml) is bubbled with carbon monoxide for 10 min. The resulting grey solids are filtered, washed with petroleum ether and air dried (61% yield).

Infrared analysis in $CHCl_3$ shows bands at 2077 (s) and 1996 (s) cm$^{-1}$.

Calcd. for $IrCl(CO)_2(Ph_3As)$: C, 40.72; H, 2.55; As, 12.70; Cl, 6.00. Found: C, 39.52; H, 2.36; As, 12.32; Cl, 5.74.

EXAMPLE 10

Preparation of $IrCl(CO)_2(Ph_3Sb)$

A suspension of $IrCl(COD)(Ph_3Sb)$ (0.5 g) and petroleum ether (25 ml) is bubbled with carbon monoxide for 10 min. The resulting brown solids are filtered, washed with petroleum ether, and air dried (60% yield). Infrared analysis in $CHCl_3$ shows bands at 2072 (s) and 1995 (s) cm$^{-1}$.

Calcd. for $IrCl(CO)_2(Ph_3Sb)$: C, 37.72; H, 2.37; Sb, 19.12; Cl, 5.56. Found: C, 36.35; H, 2.10; Sb, 18.88; Cl, 5.37.

EXAMPLE 11

Preparation of $IrCl(CO)_2(Ph_3Bi)$

A suspension of $IrCl(norbornadiene)(Ph_3Bi)$ (0.6 g) petroleum ether (25 ml) is bubbled with carbon monoxide for 10 min. The resulting tan solids were filtered, washed with petroleum ether and air dried, (50% yield). Infrared analysis in $CHCl_3$ shows bands at 2070 (s) and 1992 (s) cm$^{-1}$.

Calcd. for $IrCl(CO)_2(Ph_3Bi)$: C, 33.18; H, 2.08; Bi, 28.86; Cl, 4.89. Found: C, 32.09; H, 1.85; Bi, 27.98; Cl, 4.35.

When using tridodecylbismuthine instead of triphenylbismuthine as the biphyllic ligand, an analogous monobismuthine product is obtained.

EXAMPLE 12

Preparation of $IrCl(CO)_2[(PhO)_3P]$

A suspension of $IrCl(COD)[PhO)_3P]$ (0.5 g) and petroleum ether (25 ml) is bubbled with carbon monoxide for 10 min. The resulting black solids are filtered, washed with petroleum ether, and air dried, (68% yield). Infrared analysis in $CHCl_3$ shows bands of 2089 (s) and 2009 (s) cm$^{-1}$ in $CHCl_3$.

Calcd. for $IrCl(CO)_2[(PhO)_3P]$: C, 40.44; H, 2.54; P, 5.21; Cl, 5.96. Found: C, 38.96; H, 2.10; P, 4.96; Cl, 5.73.

EXAMPLE 13

Preparation of $IrCl(CO)_2[(BuO)_3P]$

A suspension of $IrCl(COD)[(BuO)_3P]$ (0.4 g) and petroleum ether (25 ml) is bubbled with carbon monoxide for 10 min. The resulting black solids are filtered, washed with petroleum ether, and air dried, (62% yield). Infrared analysis in $CHCl_3$ shows bands at 2084 (s) and 2003 (s) cm$^{-1}$.

Calcd. for $IrCl(CO)_2[(BuO)_3P]$: C, 31.49; H, 5.09; P, 5.80; Cl, 6.63. Found: C, 30.00; H, 4.87; P, 5.50; Cl, 6.01.

EXAMPLE 14

Preparation of $IrCl(CO)_2(Et_3P)$

A suspension of $IrCl(COD)(Et_3P)$ (0.5 g) and petroleum ether (25 ml) is bubbled with carbon monoxide for 10 min. The resulting black solids were filtered, washed with petroleum ether, and air dried (33% yield). Infrared analysis in $CHCl_3$ shows bands at 2081 (s) and 1994 (s) cm$^{-1}$.

Calcd. for $IrCl(CO)_2(Et_3P)$: C, 23.91; H, 3.76; P, 7.70; Cl, 8.82. Found: C, 23.04; H, 3.51; P, 8.01; Cl, 22.86.

EXAMPLE 15

A 300 ml autoclave is charged with the following ingredients: 0.218 g (0.4 mmole) of IrCl(CO)$_2$(Ph$_3$P) as the catalyst precursor, 4 ml of water as a reactant, and 76 ml of acetic acid.

The autoclave is pressured to 50 psig with carbon monoxide and then heated to 195°C. After reaching 195°C the autoclave is pressured to 700 psig with a 50/50 mole % CO/C$_2$H$_4$ gas blend. The reaction is carried out at constant pressure by feeding the gas blend from a high pressure reservoir into the autoclave. During the reaction time of 3 hours 960 psig of feed gas is consumed. The reaction mixture is subsequently analyzed by gas chromotography indicating:

17 wt.% propionic acid
82 wt.% acetic acid.

Thus this novel complex as well as the other iridium complexes of this invention rapidly and selectively catalyzes the hydrocarboxylation of ethylene to propionic acid.

EXAMPLE 16

A 300 ml autoclave is charged with the following ingredients: 0.253g (0.4 mmole) of IrBr(CO)$_2$(Ph$_3$As) as the catalyst precursor and 80 ml of propionic acid as the solvent and reactant.

The autoclave is pressured to 50 psig with carbon monoxide and then heated to 195°C. After reaching 195°C the autoclave is pressured to 700 psig with a 50/50 mole % CO/C$_2$H$_4$ gas blend. The reaction is carried out at constant pressure by feeding the gas blend from a high pressure reservoir into the autoclave. During the reaction time of eight hours 2160 psig of feed gas is consumed. The reaction mixture is subsequently analyzed by gas chromatography indicating:

54 wt.% propionic anhydride
46 wt.% propionic acid.

Thus this novel complex as well as the other iridium complexes of this invention rapidly and selectively catalyzes the conversion of ethylene, carbon monoxide, and propionic acid to propionic anhydride.

Various modifications of the invention, some of which have been referred to above, may be employed without departing from the spirit of the invention.

In the present invention polar solvents are the group of solvents having a dipole movement from 0.5 to 4 e.g. chloroform, dichloromethane, methanol, hexanol, nitromethane, tetrahydrofuran, chlorobenzene, nitrobenzene, 2-methoxyethanol; while the non polar solvents have a dipole movement from 0. to 0.5 e.g. cyclohexane, benzene, toluene, petroleum ether, pentane, heptane, methycyclohexane, cycloheptane, octane and dodecane.

What is claimed is:

1. Compounds having the following general formula

IrX(CO)$_2$(R$_3$M)

wherein X is selected from the group consisting of chlorine and bromine; M is selected from the group consisting of phosphorus, arsenic, antimony, and bismuth; and R is an alkyl, aryl, alkoxy, or aryloxy radical having from one to twenty carbon atoms.

2. Compounds having the following general formula

[Ir(CO)$_3$(R$_3$M)$_2$]$^+$[Ir(CO)$_2$X$_2$]$^-$ where X is selected from the group consisting of chlorine, bromine, and iodine; M is selected from the group consisting of phosphorus, arsenic, antimony, and bismuth; and R is an alkyl, aryl, alkoxy, or aryloxy radical having from one to twenty carbon atoms.

3. Compounds having the following general formula

IrI(CO)(diene)(R$_3$M)

wherein I is iodine, diene is a diolefinic hydrocarbon selected from the group consisting of 1,5-cyclooctadiene, norbornadiene, duroquinone, cyclooctatetraene, 1,5-hexadiene, 1,3-cyclohexadiene, and 2,5-dimethyl-1,5-hexadiene, M is selected from the group consisting of phosphorus, arsenic, antimony, and bismuth; and R is an alkyl, aryl, alkoxy, or aryloxy radical having from one to twenty carbon atoms.

4. Compounds having the general formula

IrI(CO)$_2$R$_3$M wherein I is iodine, M is selected from the group consisting of phosphorus, arsenic, antimony, and bismuth; and R is an alkyl, aryl, alkoxy, or aryloxy radical having from one to twenty carbon atoms.

5. A process for the preparation of the compounds of claim 1, said process comprising reacting a compound having the formula IrX(diene)(R$_3$M), wherein X, M, and R are as defined in claim 1 and diene is a diolefinic hydrocarbon selected from the group consisting of 1,5-cyclooctadiene, norbornadiene, duroquinone, cyclooctatetraene, 1,5-hexadiene, 1,3-cyclohexadiene, and 2,5-dimethyl-1,5-hexadiene, with carbon monoxide in a nonpolar aliphatic or aromatic hydrocarbon solvent.

6. A process for the preparation of the compounds of claim 2, said process comprising reacting a compound having the formula IrX(diene)(R$_3$M), wherein X, M, and R are as defined in claim 2 and diene is a diolefinic hydrocarbon selected from the group consisting of 1,5-cyclooctadiene, norbornadiene, duroquinone, cyclooctatetraene, 1,5-hexadiene, 1,3-cyclohexadiene, and 2,5-dimethyl-1,5-hexadiene, with carbon monoxide in a polar solvent.

7. A process for the preparation of the compounds of claim 3, said process comprising reacting a compound having the formula IrI(diene)R$_3$M, wherein I, M, R, and diene are as defined in claim 3, with carbon monoxide in a non-polar aliphatic hydrocarbon solvent.

8. A process for the preparation of the compounds of claim 4, said process comprising reacting a compound having the formula IrI(diene)R$_3$M, wherein I, M, and R, are as defined in claim 4, and diene is a diolefinic hydrocarbon selected from the group consisting of cyclooctadiene, norbornadiene, duroquinone, cyclooctatetraene, 1,5-hexadiene, 1,3-cyclohexadiene, and 2,5-dimethyl-1,5-hexadiene, with carbon monoxide in a non-polar aromatic hydrocarbon solvent.

9. The compound of claim 1 having the formula

IrCl(CO)$_2$(Ph$_3$P).

10. The compound of claim 1 having the formula

IrBr(CO)$_2$(Ph$_3$P)

11. The compound of claim 1 having the formula

IrCl(CO)$_2$(Me$_2$PhP)

12. The compound of claim 1 having the formula

IrCl(CO)$_2$(Ph$_3$As)

13. The compound of claim 2 having the formula

[Ir(CO)$_3$(Ph$_3$P)$_2$]$^+$[Ir(CO)$_2$Cl$_2$]$^-$

14. The compound of claim 3 having the formula

IrI(CO)(1,5-C$_8$H$_{12}$)[p-CH$_3$C$_6$H$_4$)$_3$P]

15. The compound of claim 3 having the formula

IrI(CO)(norbornadiene)(Ph$_3$P).

16. The compound of claim 4 having the formula

IrI(CO)$_2$(Ph$_3$Sb).

* * * * *